United States Patent [19]
Cao et al.

[11] Patent Number: 5,869,284
[45] Date of Patent: Feb. 9, 1999

[54] DNA ENCODING RETINOTIC ACID RECEPTOR EPSILON

[75] Inventors: Liang Cao, Monmouth Terrace, Hong Kong; Jian Ni; Robert D. Fleischmann, both of Gaithersburg, Md.

[73] Assignee: Human Genome Sciences, Inc., Rockville, Md.

[21] Appl. No.: 466,120

[22] Filed: Jun. 6, 1995

Related U.S. Application Data

[63] Continuation of PCT/US94/07266 Jun. 24, 1994.

[51] Int. Cl.$^6$ .............................. C12N 15/12; C12P 21/00; C07K 14/705
[52] U.S. Cl. .................. 435/69.1; 435/172.3; 435/252.3; 536/23.5; 530/350; 730/180; 535/1; 535/3; 535/10; 535/23; 535/35; 535/66
[58] Field of Search .......................... 536/23.5; 435/69.1, 435/172.3, 252.3; 530/350, 180; 535/1, 3, 10, 23, 55, 66; 930/180

[56] References Cited

U.S. PATENT DOCUMENTS 5,260,432 11/1993 Takaku et al. ........................... 536/23.5
5,262,300 11/1993 Evans et al. ................................. 435/6

FOREIGN PATENT DOCUMENTS 9306215  4/1993  WIPO .

OTHER PUBLICATIONS

Lohnea, D., et al., Cell, 73:643–658 (1993).
Koelle, M. R., et al., Cell, 67:59–77 (1991).
Lazoga, D., et al., Journal of Cellular Physiology, 157:90–96 (1993).
Nagpal, S., et al., The EMBO Journal, 12(6):2349–2360 (1993).

*Primary Examiner*—David L. Fitzgerald
*Assistant Examiner*—Daryl A. Basham
*Attorney, Agent, or Firm*—Elliot M. Olstein; J. G. Mullins

[57] ABSTRACT

Disclosed is a retinoic acid receptor epsilon (RARε) polynucleotide and DNA (RNA) encoding such polypeptides. Also provided is a procedure for producing such polypeptide by recombinant techniques and utilizing such polypeptide for therapeutic purposes, for example, tissue regeneration and stimulation of the immune and hematopoietic system. Also disclosed are methods of identifying ligands which stimulate the RARε. Also disclosed are diagnostic methods for detecting a mutation in the RARε receptor nucleic acid sequences and detecting a level of the soluble form of the receptors in a sample derived from a host.

20 Claims, 8 Drawing Sheets

FIG. 1A

```
AGTCCAGGTCCTGCTTGTGCTCAGCTCCAGCTCACTGGCTGCCACCGAAACTTCTGGAC     60
----+----+----+----+----+----+----+----+----+----+----+----

AGGAAACTGCACCATCCTCTCTCCCAGCAAGGGGGCTCCAGAGAACTGCCCACCCAGGA    120
----+----+----+----+----+----+----+----+----+----+----+----

AGTCTGGTGGCCTGGGGATTTGGACAGTGCCTTGGTAATGACCAGGCTCCAGGAAGAGA    180
----+----+----+----+----+----+----+----+----+----+----+----
                                                          M

TGTCCTTGTGGCTGGGGGCCCCTGTGCCTGACATTCCTCCTGACTCTGCGGTGGAGCTGT   240
----+----+----+----+----+----+----+----+----+----+----+----
 S  L  W  L  G  A  P  V  P  D  I  P  P  D  S  A  V  E  L  W

GGAAGCCAGGCGCACAGGATGCAGGCAGCCAGGGAGGCAGCAGCTGCATCCTCA         300
----+----+----+----+----+----+----+----+----+----+----+----
 K  P  G  A  Q  D  A  G  S  Q  A  Q  G  G  S  S  C  I  L  R

GAGAGGAAGCCAGGATGCCCCACTCTGCTGGGGTACTGCAGGGGTGGGGCTGGAGGCTG    360
----+----+----+----+----+----+----+----+----+----+----+----
 E  E  A  R  M  P  H  S  A  G  G  T  A  G  V  G  L  E  A  A

CAGAGCCCACAGCCCTGCTCACCAGGGCAGAGCCCCTTCAGAACCCACAGAGATCCGTC    420
----+----+----+----+----+----+----+----+----+----+----+----
 E  P  T  A  L  L  T  R  A  E  P  P  S  E  P  T  E  I  R  P

CACCAAAGCGGAAAAAGGGGCCAGCCCCCAAAATGCTGGGGAACGAGCTATGCAGCGTGT   480
----+----+----+----+----+----+----+----+----+----+----+----
 P  K  R  K  K  G  P  A  P  ,K  M  L  G  N  E  L  C  S  V  C
```

FIG. 1B

```
GTGGGGACAAGGCCTCGGGCTTCCACTACAATGTTCTGAGCTGCGAGGGCTGCAAGGAAT    540
   G  D  K  A  S  G  F  H  Y  N  V  L  S  C  E  G  C  K  E  F

TCTTCCGCGCAGCGTCATCAAGGGAGCGCACTACATCTGCCACAGTGGCGGCCACTGCC    600
   F  R  R  S  V  I  K  G  A  H  Y  I  C  H  S  G  G  H  C  P

CATGGaACACCTACATGCGTCGCAAGTGCCAGGAGTGTGTCCTGTCAGAAGAACAGATCC    660
   W  N  T  Y  M  R  R  K  C  Q  E  C  V  L  S  E  E  Q  I  R

GCCTGAAGAAACTGAAGCGGGCAAGAGGAGGAGGAACAGGTTCATGCCACATCCTTGCCCCCA   720
   L  K  K  L  K  R  Q  E  E  E  Q  V  H  A  T  S  L  P  P  R

GGGCTTCcTCACCCCCCCAAATCCTGCCCCAGTCTCAACCCGGAACAACTGGGCATGATCG    780
   A  S  S  P  P  Q  I  L  P  Q  L  N  P  E  Q  L  G  M  I  E

AGAAGCTCGTCCCTGCCCAGCAACAGTGTAACCGGCGCTCCTTTCTGACCGGCTTCGAG    840
   K  L  V  P  A  Q  Q  Q  C  N  R  R  S  F  S  D  R  L  R  V

TCACGCCTTGGCCCATGGCACCAGATCCCCATAGCCGGGAGGCCCGTCAGCAGCGCTTTG    900
   T  P  W  P  M  A  P  D  D  P  H  S  R  E  A  R  Q  Q  R  F  A
```

FIG. 1C

```
CCCACTTCACTGAGCTGGCCATCGTCTCTGTGCAGGAGATAGTTGACTTTGCTAAACAGC    960
---+---------+---------+---------+---------+---------+
 H  F  T  E  L  A  I  V  S  V  Q  E  I  V  D  F  A  K  Q  L

TACCCGGCTTCCTGCAGCTCAGCCGGGAGGACCAGATTGCCCTGCTGAAGACCTCTGCGA   1020
---+---------+---------+---------+---------+---------+
 P  G  F  L  Q  L  S  R  E  D  Q  I  A  L  L  K  T  S  A  I

TCGAGGTGATGCTTGTGGAGACATCTCGGAGGTACAACCCTGGGAGTGAGAGTATCACCT   1080
---+---------+---------+---------+---------+---------+
 E  V  M  L  V  E  T  S  R  R  Y  N  P  G  S  E  S  I  T  F

TCCTCAAGGATTTCAGTTATAACCGGGAAGACTTTGCCAAAGCAGGGCTGCAAGTGGAAT   1140
---+---------+---------+---------+---------+---------+
 L  K  D  F  S  Y  N  R  E  D  F  A  K  A  G  L  Q  V  E  F

TCATCAACCCCATCTTCGAGTTCTCCAGGGCCATGAATGAGCTGCAACTCAATGATCCCG   1200
---+---------+---------+---------+---------+---------+
 I  N  P  I  F  E  F  S  R  A  M  N  E  L  Q  L  N  D  P  E

AGTTTGCCTTGCTCATTGCTATCAGCATCTTCTCTGCAGACCGGCCCAACGTGCAGGACC   1260
---+---------+---------+---------+---------+---------+
 F  A  L  L  I  A  I  S  I  F  S  A  D  R  P  N  V  Q  D  Q

AGCTCCAGGTAGAGAGGCTGCAGCACACATATGTGGAAGCCCTGCATGCCTACGTCTCCA   1320
---+---------+---------+---------+---------+---------+
 L  Q  V  E  R  L  Q  H  T  Y  V  E  A  L  H  A  Y  V  S  I

TCCACCATCCCCATGACCGACTGATGTTCCCACGGATGCTAATGAAACTGGTGAGCCTCC   1380
---+---------+---------+---------+---------+---------+
```

FIG. 1D

```
         H  H  P  H  D  R  L  M  F  P  P  R  M  L  M  K  L  V  S  L  R
      GGaCCCTGAGCAGCGTCCACTCAGAGCAAGTGTTTGCACTGGTCTGCAGGACAAAAAGC       1440
         T  L  S  S  V  H  S  E  Q  V  F  A  L  R  L  Q  D  K  K  L
      TCCCACCGCTGCTCTCTGAGATCTGGGATGTGCACGAATGACTGTTCTGTCCCCATATTT       1500
         P  P  L  L  S  E  I  W  D  V  H  E
      TCTGTTTCTTGGCCGATGGCTGAGGCCTGGTGGCTGCCTCCTAGAAGTGGAACAGACT        1560
      GAGAAGGGCAAACATTCCTGGGAGCTGGGAAAGGAGATCCTCCCGTGGCATTAAAAGAGA      1620
      GTCAAAGGGTAAAAAAAAAAAAAAAAAA       1649
```

FIG. 2A

```
           1
RARY       ........ ...MYDCMET FAPGPRRLYG AAGPGAGLL. ....RRATGG    50
RARε       MSLWLGAPVP DIPPDSAVEL WKPGAQDAGS QAQGGSSCIL REEARMPHSA 51                                                    100
RARY       SCFAGLESFA WPQPASLQSV ETQSTSSEEM VPSSPSPPPP PRV.YKPCFV
RARε       GGTAGVGLEA AEPTALLTRA EPPSEPTEIR PPKRKKGPAP KMLGNELCSV

101            I: modulator region                    150
RARY       CNDKSSGYHY GVSSCEGCKG FFRRSIQKNM VYTCHRDKNC IINKVTRNRC
RARε       CGDKASGFHY NVLSCEGCKE FFRRSVIKGA HYICHSGGHC PWNTYMRRKC 151                                                   200
RARY       QYCRLQKCFE VGMSKEAVRN DRNKKKKE.. ......VKE EGSPDSY.EL
RARε       Q........E CVLSEEQIRL KKLKRQEEEQ VHATSLPPRA SSPPQILPQL 201                                                   250
RARY       SPQLEELITK VSKAHQE.TF PSLCQLGKYT TNSSA..DHR VQLDLGLWDK
RARε       NPEQLGMIEK LVPAQQQCNR RSFSDRLRVT PWPMAPDPHS REARQQRFAH
```

FIG. 2B

```
              II: DNA binding region
         251                                                          300
RARγ     FSELATKCII KIVEFAKRLP GFTGLSIADQ ITLLKAACLD ILMLRICTRY
RARε     ETELAIVSVQ EIVDFAKQLP GFLQLSREDQ IALLKTSAIE VMLVETSRRY 301                                                          350
RARγ     TPEQDTMTFS DGLTLNRTQM HNAGF.GPLT DLVFAFAGQL LPLEMDDTET
RARε     NPGSESITFL KDFSYNREDF AKAGLQVEFI NPIFEFSRAM NELQLNDEE III. ligand binding region
         351                                                          400
RARγ     GLLSAICLIC GDRMDLEEPE KVDKLQEPLL EALRLYARRR RPSQPYMFPR
RARε     ALLIAISIFS ADRPNVQDQL QVERLQHTYV EALHAYVSIH HPHDRLMFPR 401                                                          450
RARγ     MLMKITDLRG ISTKGAERAI TLKMEIPGPM PPLIREMLEN PEMFEDDSSQ
RARε     MLMKLVSLRT LSSVHSEQVF ALRLQ.DKKL PPLLSEIWDV HE.........

451        476
RARγ     PGPHPNASSE DEVPGGQGKG GLKSPA
RARε
```

1. ovary
2. testes
3. gall bladder
4. kidney
5. liver
6. lung
7. spleen
8. prostate
9. hippocampus
10. heart
11. pancreas
12. placenta
13. thymus M: Marker TI: Thrombin Inhibitor RAR: retinoic acid receptor

DNA ENCODING RETINOTIC ACID RECEPTOR EPSILON

This application is entitled to priority benefits under 35 U.S.C §120 for the information set forth in PCT/US94/07266, filed Jun. 24, 1994.

This invention relates to newly identified polynucleotides, polypeptides encoded by such polynucleotides, the use of such polynucleotides and polypeptides, as well as the production of such polynucleotides and polypeptides. More particularly, the polypeptide of the present invention is Retinoic Acid Receptor Epsilon (RARε). The invention also relates to inhibiting the action of such polypeptides.

Retinoids (Vitamin A derivatives) are crucial for normal growth, vision, maintenance of numerous tissues, reproduction and overall survival (Wolbach, S. B., *J. Exp. Med.*, 42:753–777 (1925)). In addition, offspring of Vitamin A deficient (VAD) dams exhibit a number of developmental defects, indicating that retinoids are also important during embryogenesis (Wilson, J. G., et al., *Am. J. Anat.*, 92:189–217 (1953)). The effects of Vitamin A deficiency in fetuses and young and adult animals can be prevented and/or reversed by retinoic acid (RA) administration (Wilson, J. G., et al., *Am. J. Anat.*, 92:189–217 (1953)). The dramatic teratogenic effects of maternal RA administration on mammalian embryos and the spectacular effects of topical administration of retinoids on embryonic development of vertebrates and limb-regeneration in amphibians have markedly contributed to the belief that RA could, in fact, be a morphogen (conferring positional information during development) and may also play a critical role during organogenesis (Tabin, C. J., *Cell*, 66:199–217 (1991)).

Retinoids are also crucial for normal growth, vision, maintenance of numerous tissues, reproduction and overall survival (Wolbach, S. B. and Howe, P. R., J. Exp. Med., 42:753–777 (1925)).

It is thought that the effects of the RA signal are mediated through two families of receptors that belong to the superfamily of ligand-inducible transcriptional regulatory factors, which includes steroid-thyroid hormone and vitamin D3 receptors (Evans, R. M., *Science*, 240:889–895 (1988)).

The retinoic acid receptor genes belong to the superfamily of genes known as the steroid hormone receptor family. All genes in this family can be divided into discrete regions or domains that are sometimes referred to as regions A/B, C, D, E, and F. The C region encodes the DNA-binding domain, the E region encodes the ligand-binding domain and the F region encodes the carboxy-terminus domain. The D region is believed to function as a "hinge". The function of the A/B (or N-terminus) region is not entirely clear but it may be involved with enhancement and repression of receptor transcription activity. (Hollenberg et al., *Cell*, 55:899–906 (1988)).

The RA receptor (RAR) family (RARα, β and γ and their isoforms) are activated by both all-trans and non-cis RA. RARδ has also been cloned (Mech, Dev., 40:99–112 (1993)). Within a given species, the DNA-binding region and the ligand-binding region domains of the three RAR types are highly similar, whereas the C-terminal region and the middle region exhibit no or little similarity. The amino acid sequences of the three RAR types are also notably different in their B regions, and their main isoforms (α1 and α2, β1 to β4, γ1 and γ2 and δ1 and δ2) further differ in their N-terminal A regions (Leid, M. et al., *Trends Biochem. Sci.*, 17:427–433 (1992)).

RARγ mutant mice exhibit growth deficiency, early lethality, and male sterility due to squamous metaplasia of the seminal vesicles and prostate (Lohnes, D. et al., Cell, 73:643–658 (1993)).

RARγ transcripts are found in precartilaginous condensations, with subsequent restriction to cartilage and differentiating squamous keratinizing epithelia, regardless of their embryonic origin (Dolle, P. et al., *Nature*, 342:702–705 (1989)). These observations suggest a role for RARγ in morphogenesis and chondrogenesis (Dolle et al., *Development*, 100:1133–1151 (1990)).

The DNA sequence and polypeptide encoded by such DNA sequence of the present invention belongs to the retinoic acid receptor family and is most homologous to retinoic acid receptor gamma. Both modulator and the DNA binding domains share the highest homology with the corresponding parts of the ecdysone receptor of Drosophila. The ecdysone receptor plays an important role during development.

In accordance with one aspect of the present invention, there is provided a novel mature polypeptide, as well as biologically active and diagnostically or therapeutically useful fragments, analogs and derivatives thereof. The polypeptide of the present invention is of human origin.

In accordance with another aspect of the present invention, there are provided isolated nucleic acid molecules encoding a polypeptide of the present invention including mRNAs, DNAs, cDNAs, genomic DNAs as well as analogs and biologically active and diagnostically or therapeutically useful fragments thereof.

In accordance with yet a further aspect of the present invention, there is provided a process for producing such polypeptide by recombinant techniques comprising culturing recombinant prokaryotic and/or eukaryotic host cells, containing a nucleic acid sequence encoding a polypeptide of the present invention, under conditions promoting expression of said protein and subsequent recovery of said protein.

In accordance with yet a further aspect of the present invention, there is provided a process for utilizing such polypeptide, or polynucleotide encoding such polypeptide for therapeutic purposes, for example, to identify its novel hormone, DNA binding sites, gene targets and tissue specificity, which provide therapeutic targets for stimulating development, differentiation, tissue regeneration, reproduction and stimulation of immune and hematopoietic systems.

In accordance with yet a further aspect of the present invention, there is also provided nucleic acid probes comprising nucleic acid molecules of sufficient length to specifically hybridize to a nucleic acid sequence of the present invention.

In accordance with yet a further aspect of the present invention, there are provided antibodies against such polypeptides.

In accordance with still another aspect of the present invention, there are provided diagnostic assays for detecting diseases or susceptibility to diseases related to mutations in the nucleic acid sequences encoding a polypeptide of the present invention.

In accordance with yet a further aspect of the present invention, there is provided a process for utilizing such polypeptides, or polynucleotides encoding such polypeptides, for in vitro purposes related to scientific research, for example, synthesis of DNA and manufacture of DNA vectors.

These and other aspects of the present invention should be apparent to those skilled in the art from the teachings herein.

BRIEF DESCRIPTION OF THE DRAWINGS

The following drawings are illustrative of embodiments of the invention and are not meant to limit the scope of the invention as encompassed by the claims.

FIG. 1 depicts the cDNA (SEQ ID NO:1) and corresponding deduced amino acid sequence (SEQ ID NO:2) of the putative mature polypeptide of the present invention. The standard one letter abbreviation for amino acids is used. Sequencing was performed using a 373 automated DNA sequencer (Applied Biosystems, Inc.).

FIG. 2 illustrates the high homology between the polypeptide of the present invention and RARγ at the DNA binding region and ligand binding region.

In accordance with an aspect of the present invention, there is provided an isolated nucleic acid (polynucleotide) which encodes for the mature polypeptide having the deduced amino acid sequence of FIG. 1 (SEQ ID NO:2) or for the mature polypeptide encoded by the cDNA of the clone deposited as ATCC Deposit No. 75754 on Mar. 18, 1994.

The ATCC number referred to above is directed to a biological deposit with the ATCC, 12301 Parklawn Drive, Rockville, Md. 20852. The strain is being maintained under the terms of the Budapest Treaty and will be made available to a patent office signatory to the Budapest Treaty.

Figure 5:
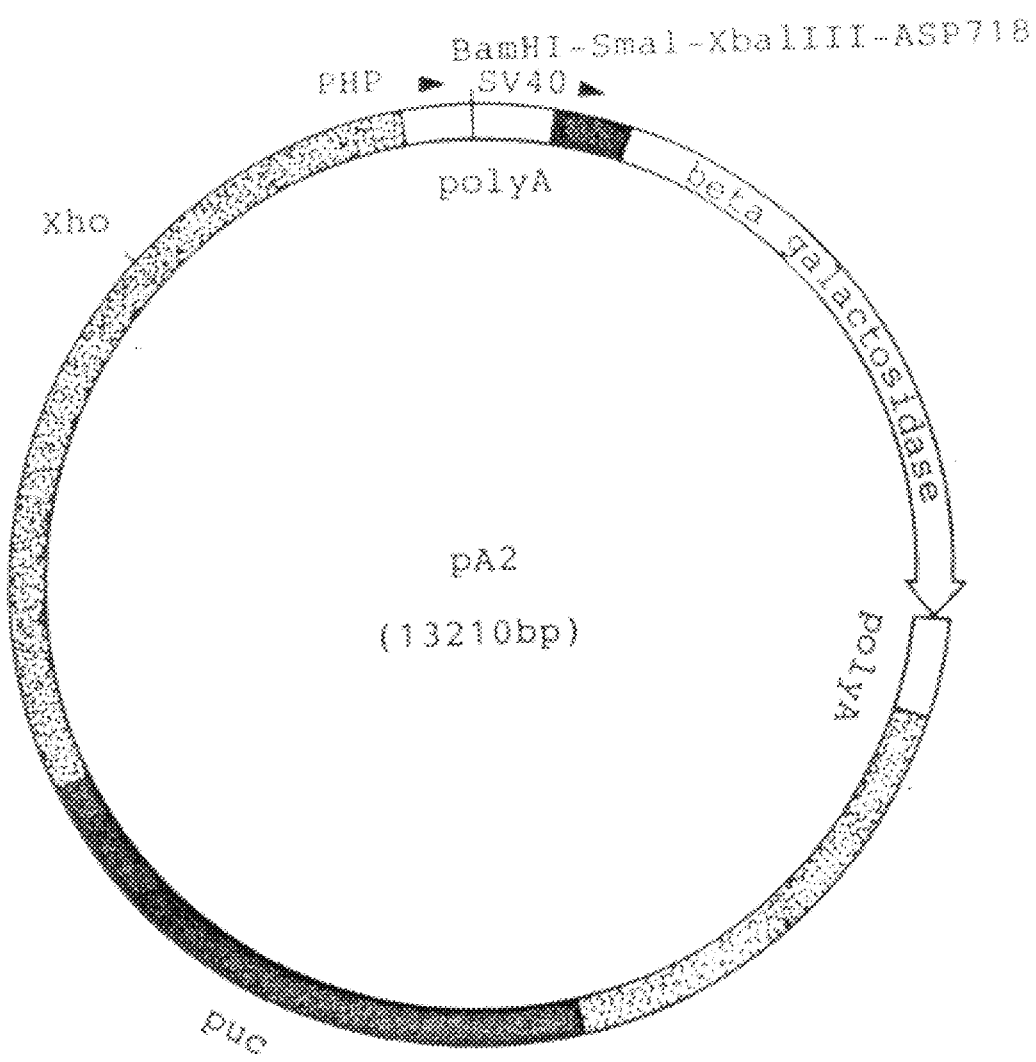
FIG. 5 illustrates the baculovirus transfer plasmid pA2 used for expression of the polypeptide of the present invention.

A polynucleotide encoding a polypeptide of the present invention may be obtained from testes, spleen and thymus. The polynucleotide of this invention was discovered in a cDNA library derived from human adult lung. It is structurally related to the retinoic acid receptor family. It contains an open reading frame encoding a protein of approximately 433 amino acid residues. The protein exhibits the highest degree of homology to retinoic acid receptor gamma with 48% identity and 58% similarity over a 70 amino acid stretch of the modulator region. Similarly, the DNA binding region and ligand binding region are also highly homologous to retinoid acid receptor gamma (FIG. 5).

The polynucleotide of the present invention may be in the form of RNA or in the form of DNA, which DNA includes cDNA, genomic DNA, and synthetic DNA. The DNA may be double-stranded or single-stranded, and if single stranded may be the coding strand or non-coding (anti-sense) strand. The coding sequence which encodes the mature polypeptide may be identical to the coding sequence shown in FIG. 1 (SEQ ID NO:1) or that of the deposited clone or may be a different coding sequence which coding sequence, as a result of the redundancy or degeneracy of the genetic code, encodes the same mature polypeptide as the DNA of FIG. 1 (SEQ ID NO:1) or the deposited cDNA.

The polynucleotide which encodes for the mature polypeptide of FIG. 1 (SEQ ID NO:2) or for the mature polypeptide encoded by the deposited CDNA may include: only the coding sequence for the mature polypeptide; the coding sequence for the mature polypeptide and additional coding sequence; the coding sequence for the mature polypeptide (and optionally additional coding sequence) and non-coding sequence, such as introns or non-coding sequence 5' and/or 3' of the coding sequence for the mature polypeptide.

Thus, the term "polynucleotide encoding a polypeptide" encompasses a polynucleotide which includes only coding sequence for the polypeptide as well as a polynucleotide which includes additional coding and/or non-coding sequence.

The present invention further relates to variants of the hereinabove described polynucleotides which encode for fragments, analogs and derivatives of the polypeptide having the deduced amino acid sequence of FIG. 1 (SEQ ID NO:2) or the polypeptide encoded by the cDNA of the deposited clone. The variant of the polynucleotide may be a naturally occurring allelic variant of the polynucleotide or a non-naturally occurring variant of the polynucleotide.

Thus, the present invention includes polynucleotides encoding the same mature polypeptide as shown in FIG. 1 (SEQ ID NO:2) or the same mature polypeptide encoded by the cDNA of the deposited clone as well as variants of such polynucleotides which variants encode for a fragment, derivative or analog of the polypeptide of FIG. 1 (SEQ ID NO:2) or the polypeptide encoded by the cDNA of the deposited clone. Such nucleotide variants include deletion variants, substitution variants and addition or insertion variants.

As hereinabove indicated, the polynucleotide may have a coding sequence which is a naturally occurring allelic variant of the coding sequence shown in FIG. 1 (SEQ ID NO:1) or of the coding sequence of the deposited clone. As known in the art, an allelic variant is an alternate form of a polynucleotide sequence which may have a substitution, deletion or addition of one or more nucleotides, which does not substantially alter the function of the encoded polypeptide.

The polynucleotides may also encode for a soluble form of the receptor polypeptide of the present invention which is the extracellular portion of the polypeptide which has been cleaved from the TM and intracellular domain of the full-length polypeptide of the present invention.

The polynucleotides of the present invention may also have the coding sequence fused in frame to a marker sequence which allows for purification of the polypeptide of the present invention. The marker sequence may be a hexahistidine tag supplied by a pQE-9 vector to provide for purification of the mature polypeptide fused to the marker in the case of a bacterial host, or, for example, the marker sequence may be a hemagglutinin (HA) tag when a mammalian host, e.g. COS-7 cells, is used. The HA tag corresponds to an epitope derived from the influenza hemagglutinin protein (Wilson, I., et al., Cell, 37:767 (1984)).

The present invention further relates to polynucleotides which hybridize to the hereinabove-described sequences if there is at least 70%, preferably at least 90%, and more preferably at least 95% identity between the sequences. The present invention particularly relates to polynucleotides which hybridize under stringent conditions to the hereinabove-described polynucleotides. As herein used, the term "stringent conditions" means hybridization will occur only if there is at least 95% and preferably at least 97% identity between the sequences. The polynucleotides which hybridize to the hereinabove described polynucleotides in a preferred embodiment encode polypeptides which either retain substantially the same biological function or activity as the mature polypeptide encoded by the cDNAs of FIG. 1 (SEQ ID NO:1) or the deposited cDNA(s), i.e. function as a soluble receptor by retaining the ability to bind the ligands for the receptor even though the polypeptide does not function as a membrane bound receptor, for example, by eliciting a second messenger response.

Alternatively, the polynucleotides may have at least 20 bases, preferably 30 bases and more preferably at least 50 bases which hybridize to a polynucleotide of the present invention and which have an identity thereto, as hereinabove described, and which may or may not retain activity. For example, such polynucleotides may be employed as probes for the polynucleotide of SEQ ID NO: 1, or for variants thereof, for example, for recovery of the polynucleotide or as a diagnostic probe or as a PCR primer.

Thus, the present invention is directed to polynucleotides having at least a 70% identity, preferably at least 90% and more preferably at least a 95% identity to a polynucleotide which encodes the polypeptide of SEQ ID NO:2 as well as fragments thereof, which fragments have at least 30 bases and preferably at least 50 bases and to polypeptides encoded by such polynucleotides.

The term "gene" means the segment of DNA involved in producing a polypeptide chain; it includes regions preceding and following the coding region "leader and trailer" as well as intervening sequences (introns) between individual coding segments (exons).

Fragments of the genes may be employed as a hybridization probe for a cDNA library to isolate other genes which have a high sequence similarity to the genes of the present invention, or which have similar biological activity. Probes of this type are at least 20 bases, preferably at least 30 bases and most preferably at least 50 bases or more. The probe may also be used to identify a cDNA clone corresponding to a full length transcript and a genomic clone or clones that contain the complete gene of the present invention including regulatory and promoter regions, exons and introns. An example of a screen of this type comprises isolating the coding region of the gene by using the known DNA sequence to synthesize an oligonucleotide probe. Labeled oligonucleotides having a sequence complementary to that of the genes of the present invention are used to screen a library of human cDNA, genomic DNA or mRNA to determine which members of the library the probe hybridizes to.

The deposit(s) referred to herein will be maintained under the terms of the Budapest Treaty on the International Recognition of the Deposit of Micro-organisms for purposes of Patent Procedure. These deposits are provided merely as convenience to those of skill in the art and are not an admission that a deposit is required under 35 U.S.C. §112. The sequence of the polynucleotides contained in the deposited materials, as well as the amino acid sequence of the polypeptides encoded thereby, are incorporated herein by reference and are controlling in the event of any conflict with any description of sequences herein. A license may be required to make, use or sell the deposited materials, and no such license is hereby granted.

The present invention further relates to a receptor polypeptide which has the deduced amino acid sequence of FIG. 1 (SEQ ID NO:2) or which has the amino acid sequence encoded by the deposited cDNA, as well as fragments, analogs and derivatives of such polypeptide.

The terms "fragment," "derivative" and "analog" when referring to the polypeptide of FIG. 1 (SEQ ID NO:2) or that encoded by the deposited cDNA, means a polypeptide which either retains substantially the same biological function or activity as such polypeptide, i.e. functions as a receptor, or retains the ability to bind the ligand for the receptor even though the polypeptide does not function as an RARε receptor, for example, a soluble form of the receptor.

The polypeptide of the present invention may be a recombinant polypeptide, a natural polypeptide or a synthetic polypeptide, preferably a recombinant polypeptide.

The fragment, derivative or analog of the polypeptide of FIG. 1 (SEQ ID NO:2) or that encoded by the deposited cDNA may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues includes a substituent group, or (iii) one in which the mature polypeptide is fused with another compound, such as a compound to increase the half-life of the polypeptide (for example, polyethylene glycol), or (iv) one in which the additional amino acids are fused to the mature polypeptide which are employed for purification of the mature polypeptide or a proprotein sequence or (v) one in which a fragment of the polypeptide is soluble, i.e. not membrane bound, yet still binds ligands to the membrane bound receptor. Such fragments, derivatives and analogs are deemed to be within the scope of those skilled in the art from the teachings herein.

The polypeptides and polynucleotides of the present invention are preferably provided in an isolated form, and preferably are purified to homogeneity.

The polypeptides of the present invention include the polypeptide of SEQ ID NO:2 (in particular the mature polypeptide) as well as polypeptides which have at least 70% similarity (preferably at least a 70% identity) to the polypeptide of SEQ ID NO:2 and more preferably at least a 90% similarity (more preferably at least a 90% identity) to the polypeptide of SEQ ID NO:2 and still more preferably at least a 95% similarity (still more preferably at least a 95% identity) to the polypeptide of SEQ ID NO:2 and also includes portions of such polypeptides with such portion of the polypeptide generally containing at least 30 amino acids and more preferably at least 50 amino acids.

As known in the art "similarity" between two polypeptides is determined by comparing the amino acid sequence and its conserved amino acid substitutes of one polypeptide to the sequence of a second polypeptide.

Fragments or portions of the polypeptides of the present invention may be employed for producing the corresponding full-length polypeptide by peptide synthesis, therefore, the fragments may be employed as intermediates for producing the full-length polypeptides. Fragments or portions of the polynucleotides of the present invention may be used to synthesize full-length polynucleotides of the present invention.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated. Such polynucleotides could be part of a vector and/or such polynucleotides or polypeptides could be part of a composition, and still be isolated in that such vector or composition is not part of its natural environment.

The present invention also relates to vectors which include polynucleotides of the present invention, host cells which are genetically engineered with vectors of the invention and the production of polypeptides of the invention by recombinant techniques.

Host cells are genetically engineered (transduced or transformed or transfected) with the vectors of this invention which may be, for example, a cloning vector or an expression vector. The vector may be, for example, in the form of a plasmid, a viral particle, a phage, etc. The engineered host cells can be cultured in conventional nutrient media modified as appropriate for activating promoters, selecting transformants or amplifying the RARε genes. The culture conditions, such as temperature, pH and the like, are those previously used with the host cell selected for expression, and will be apparent to the ordinarily skilled artisan.

The polynucleotides of the present invention may be employed for producing polypeptides by recombinant techniques. Thus, for example, the polynucleotide may be included in any one of a variety of expression vectors for expressing a polypeptide. Such vectors include chromosomal, nonchromosomal and synthetic DNA sequences, e.g., derivatives of SV40; bacterial plasmids; phage DNA; baculovirus; yeast plasmids; vectors derived from combinations of plasmids and phage DNA, viral DNA such as vaccinia, adenovirus, fowl pox virus, and pseudorabies. However, any other vector may be used as long as it is replicable and viable in the host.

The appropriate DNA sequence may be inserted into the vector by a variety of procedures. In general, the DNA sequence is inserted into an appropriate restriction endonuclease site(s) by procedures known in the art. Such procedures and others are deemed to be within the scope of those skilled in the art.

The DNA sequence in the expression vector is operatively linked to an appropriate expression control sequence(s) (promoter) to direct MRNA synthesis. As representative examples of such promoters, there may be mentioned: LTR or SV40 promoter, the E. coli. lac or trp, the phage lambda $P_L$ promoter and other promoters known to control expression of genes in prokaryotic or eukaryotic cells or their viruses. The expression vector also contains a ribosome binding site for translation initiation and a transcription terminator. The vector may also include appropriate sequences for amplifying expression.

In addition, the expression vectors preferably contain one or more selectable marker genes to provide a phenotypic trait for selection of transformed host cells such as dihydrofolate reductase or neomycin resistance for eukaryotic cell culture, or such as tetracycline or ampicillin resistance in E. coli.

The vector containing the appropriate DNA sequence as hereinabove described, as well as an appropriate promoter or control sequence, may be employed to transform an appropriate host to permit the host to express the protein.

As representative examples of appropriate hosts, there may be mentioned: bacterial cells, such as E. coli, Streptomyces, Salmonella typhimurium; fungal cells, such as yeast; insect cells such as Drosophila and Spodoptera Sf9; animal cells such as CHO, COS or Bowes melanoma; plant cells, etc. The selection of an appropriate host is deemed to be within the scope of those skilled in the art from the teachings herein.

More particularly, the present invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art, and are commercially available. The following vectors are provided by way of example. Bacterial: pQE70, pQE60, pQE-9 (Qiagen), pbs, pD10, phagescript, psiX174, pbluescript SK, pbsks, pNH8A, pNH16a, pNH18A, pNH46A (Stratagene); ptrc99a, pKK223-3, pKK233-3, pDR540, pRIT5 (Pharmacia), pRS and pGEM. Eukaryotic: pWLNEO, pSV2CAT, pOG44, pXT1, pSG (Stratagene) pSVK3, pBPV, pMSG, pSVL (Pharmacia). However, any other plasmid or vector may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In a further embodiment, the present invention relates to host cells containing the above-described constructs. The host cell can be a higher eukaryotic cell, such as a mammalian cell, or a lower eukaryotic cell, such as a yeast cell, or the host cell can be a prokaryotic cell, such as a bacterial cell. Introduction of the construct into the host cell can be effected by calcium phosphate transfection, DEAE-Dextran mediated transfection, or electroporation. (Davis, L., Dibner, M., Battey, I., Basic Methods in Molecular Biology, (1986)).

The constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook, et al., Molecular Cloning: A Laboratory Manual, Second Edition, Cold Spring Harbor, N. Y., (1989), the disclosure of which is hereby incorporated by reference.

Transcription of the DNA encoding the polypeptides of the present invention by higher eukaryotes is increased by inserting an enhancer sequence into the vector. Enhancers are cis-acting elements of DNA, usually about from 10 to 300 bp that act on a promoter to increase its transcription. Examples including the SV40 enhancer on the late side of the replication origin bp 100 to 270, a cytomegalovirus early promoter enhancer, the polyoma enhancer on the late side of the replication origin, and adenovirus enhancers.

Generally, recombinant expression vectors will include origins of replication and selectable markers permitting transformation of the host cell, e.g., the ampicillin resistance gene of E. coli and S. cerevisiae TRP1 gene, and a promoter derived from a highly-expressed gene to direct transcription of a downstream structural sequence. Such promoters can be derived from operons encoding glycolytic enzymes such as 3-phosphoglycerate kinase (PGK), α-factor, acid phosphatase, or heat shock proteins, among others. The heterologous structural sequence is assembled in appropriate phase with translation initiation and termination sequences, and preferably, a leader sequence capable of directing secretion of translated protein into the periplasmic space or extracellular medium. Optionally, the heterologous sequence can encode a fusion protein including an N-terminal identification peptide imparting desired characteristics, e.g., stabilization or simplified purification of expressed recombinant product.

Useful expression vectors for bacterial use are constructed by inserting a structural DNA sequence encoding a desired protein together with suitable translation initiation and termination signals in operable reading phase with a functional promoter. The vector will comprise one or more phenotypic selectable markers and an origin of replication to ensure maintenance of the vector and to, if desirable, provide amplification within the host. Suitable prokaryotic hosts for transformation include E. coli, Bacillus subtilis, Salmonella typhimurium and various species within the genera Pseudomonas, Streptomyces, and Staphylococcus, although others may also be employed as a matter of choice.

As a representative but nonlimiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). These pBR322 "backbone" sections are combined with an appropriate promoter and the structural sequence to be expressed.

Following transformation of a suitable host strain and growth of the host strain to an appropriate cell density, the selected promoter is induced by appropriate means (e.g., temperature shift or chemical induction) and cells are cultured for an additional period.

Cells are typically harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents, such methods are well know to those skilled in the art.

Various mammalian cell culture systems can also be employed to express recombinant protein. Examples of mammalian expression systems include the COS-7 lines of monkey kidney fibroblasts, described by Gluzman, Cell, 23:175 (1981), and other cell lines capable of expressing a compatible vector, for example, the C127, 3T3, CHO, HeLa and BHK cell lines. Mammalian expression vectors will comprise an origin of replication, a suitable promoter and enhancer, and also any necessary ribosome binding sites, polyadenylation site, splice donor and acceptor sites, transcriptional termination sequences, and 5' flanking nontranscribed sequences. DNA sequences derived from the SV40 splice, and polyadenylation sites may be used to provide the required nontranscribed genetic elements.

The RARε polypeptides can be recovered and purified from recombinant cell cultures by methods including ammonium sulfate or ethanol precipitation, acid extraction, anion or cation exchange chromatography, phosphocellulose chromatography, hydrophobic interaction chromatography, affinity chromatography hydroxylapatite chromatography and lectin chromatography. It is preferred to have low concentrations (approximately 0.15–5 mM) of calcium ion present during purification. (Price et al., J. Biol. Chem., 244:917 (1969)). Protein refolding steps can be used, as necessary, in completing configuration of the mature protein. Finally, high performance liquid chromatography (HPLC) can be employed for final purification steps.

The polypeptides of the present invention may be a naturally purified product, or a product of chemical synthetic procedures, or produced by recombinant techniques from a prokaryotic or eukaryotic host (for example, by bacterial, yeast, higher plant, insect and mammalian cells in culture). Depending upon the host employed in a recombinant production procedure, the polypeptides of the present invention may be glycosylated or may be non-glycosylated. Polypeptides of the invention may also include an initial methionine amino acid residue.

The RARε receptor may be employed for the identification of its novel hormones, DNA binding sites, gene targets and tissue specificity. The RARε polypeptide may also be employed as a therapeutic target for tissue regeneration, reproduction, stimulation of the immune and hematopoietic system, and for the treatment of male sterility. This is particularly important since RAR mutant mice exhibited the previously stated abnormalities. Accordingly, the RARε receptor may be employed to treat these disorders.

The RARε polypeptide may also be employed for screening of putative hormone molecules, such as steroid agonists that can modulate the hormone response mediated through this receptor. To assay for these and other ligands for the RARε, for example, the gene encoding RARε binding sites is cloned in the pRS eukaryotic expression vector (Giguere et al., Cell, 46:645 (1986)) producing pRShRARε. The plasmid is then introduced into monkey kidney CV-1 cells via calcium-phosphate transfection together with a reporter plasmid DELTA MTV-TRE sub p-CAT. TRE means thyroid receptor response element and TRE sub p is a TRE that has been engineered to maximize the palindorminicity of this element. As a control, pRSerbA sup-1 (encodes no protein, stands as a negative control), is also examined. The transfected cells are incubated in the presence or absence of 100 nM retinoic acid, or other potential ligands, for 36 hours, and the induced CAT activities were analyzed by chromatography. The results will indicate which ligands bind to RARε.

This invention further provides a method of screening compounds to identify those which enhance (agonists) interaction of ligands to the RARε. As an example, a reporter plasmid and pRShRARε are introduced into monkey cells as discussed above. The transfected cells are then incubated with a candidate compound under conditions favoring binding of known ligands, for example, retinoic acid. The reporter gene can be a CAT or luciferase gene whose activities with respect to the interaction of ligand and receptor are capable of being measured (Promega Technical Bulletin No. 126, July, 1993). Transfection systems are useful as living cell cultures for competitive binding assays between known or candidate drugs and ligands which bind to the receptor and which are labeled by radioactive, spectroscopic or other reagents. A transfection system constitutes a "drug discovery system" useful for the identification of natural or synthetic compounds with potential for drug development that can be further modified or used directly as therapeutic compounds to activate or inhibit the natural functions of the human RARε. The transfection system is also useful for determining the affinity and efficacy of known drugs at the human RARε sites.

The agonist compounds and soluble form of the receptor may be employed in combination with a suitable pharmaceutical carrier. Such compositions comprise a therapeutically effective amount of the compound, and a pharmaceutically acceptable carrier or excipient. Such a carrier includes but is not limited to saline, buffered saline, dextrose, water, glycerol, ethanol, and combinations thereof. The formulation should suit the mode of administration.

The invention also provides a pharmaceutical pack or kit comprising one or more containers filled with one or more of the ingredients of the pharmaceutical compositions of the invention. Associated with such container(s) can be a notice in the form prescribed by a governmental agency regulating the manufacture, use or sale of pharmaceuticals or biological products, which notice reflects approval by the agency of manufacture, use or sale for human administration. In addition, the pharmaceutical compositions of the present invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. The pharmaceutical compositions are administered in an amount which is effective for treating and/or prophylaxis of the specific indication. In general, the pharmaceutical compositions will be administered in an amount of at least about 10 μg/kg body weight and in most cases they will be administered in an amount not in excess of about 8 mg/Kg body weight per day. In most cases, the dosage is from about 10 μg/kg to about 1 mg/kg body weight daily, taking into account the routes of administration, symptoms, etc.

The soluble form of the receptor and agonists which are polypeptides may also be employed in accordance with the present invention by expression of such polypeptides in vivo, which is often referred to as "gene therapy." Thus, for example, cells from a patient may be engineered with a polynucleotide (DNA or RNA) encoding a polypeptide ex vivo, with the engineered cells then being provided to a patient to be treated with the polypeptide. Such methods are well-known in the art. For example, cells may be engineered by procedures known in the art by use of a retroviral particle containing RNA encoding a polypeptide of the present invention.

Similarly, cells may be engineered in vivo for expression of a polypeptide in vivo by, for example, procedures known in the art. As known in the art, a producer cell for producing a retroviral particle containing RNA encoding the polypeptide of the present invention may be administered to a patient for engineering cells in vivo and expression of the polypeptide in vivo. These and other methods for administering a polypeptide of the present invention by such method should be apparent to those skilled in the art from the teachings of the present invention. For example, the expression vehicle for engineering cells may be other than a retrovirus, for example, an adenovirus which may be used to engineer cells in vivo after combination with a suitable delivery vehicle.

Retroviruses from which the retroviral plasmid vectors hereinabove mentioned may be derived include, but are not limited to, Moloney Murine Leukemia Virus, spleen necrosis virus, retroviruses such as Rous Sarcoma Virus, Harvey Sarcoma Virus, avian leukosis virus, gibbon ape leukemia virus, human immunodeficiency virus, adenovirus, Myeloproliferative Sarcoma Virus, and mammary tumor virus. In one embodiment, the retroviral plasmid vector is derived from Moloney Murine Leukemia Virus.

The vector includes one or more promoters. Suitable promoters which may be employed include, but are not limited to, the retroviral LTR; the SV40 promoter; and the human cytomegalovirus (CMV) promoter described in Miller, et al., Biotechniques, Vol. 7, No. 9, 980–990 (1989), or any other promoter (e.g., cellular promoters such as eukaryotic cellular promoters including, but not limited to, the histone, pol III, and β-actin promoters). Other viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention is under the control of a suitable promoter. Suitable promoters which may be employed include, but are not limited to, adenoviral promoters, such as the adenoviral major late promoter; or hetorologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs hereinabove described); the β-actin promoter; and human growth hormone promoters. The promoter also may be the native promoter which controls the genes encoding the polypeptides.

The retroviral plasmid vector is employed to transduce packaging cell lines to form producer cell lines. Examples of packaging cells which may be transfected include, but are not limited to, the PE501, PA317, ψ-2, ψ-AM, PA12, T19–14X, VT-19–17-H2, ψCRE, ψCRIP, GP+E-86, GP+envAm12, and DAN cell lines as described in Miller, Human Gene Therapy, Vol. 1, pgs. 5–14 (1990), which is incorporated herein by reference in its entirety. The vector may transduce the packaging cells through any means known in the art. Such means include, but are not limited to, electroporation, the use of liposomes, and CaPO$_4$ precipitation. In one alternative, the retroviral plasmid vector may be encapsulated into a liposome, or coupled to a lipid, and then administered to a host.

The producer cell line generates infectious retroviral vector particles which include the nucleic acid sequence(s) encoding the polypeptides. Such retroviral vector particles then may be employed, to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

This invention also provides a method of detecting expression of an RARε receptor polypeptide of the present invention on the surface of a cell by detecting the presence of MRNA coding for the receptor which comprises obtaining total mRNA from the cell and contacting the MRNA so obtained with a nucleic acid probe comprising a nucleic acid molecule of at least 10 nucleotides capable of specifically hybridizing with a sequence included within the sequence of a nucleic acid molecule encoding the receptor under hybridizing conditions, detecting the presence of mRNA hybridized to the probe, and thereby detecting the expression of the receptor by the cell.

The present invention also provides a method for identifying receptors related to the receptor polypeptides of the present invention. These related receptors may be identified by homology to a receptor polypeptide of the present invention, by low stringency cross hybridization, or by identifying receptors that interact with related natural or synthetic ligands and or elicit similar behaviors after genetic or pharmacological blockade of the receptor polypeptides of the present invention.

The present invention also contemplates the use of the genes of the present invention as a diagnostic, for example, some diseases result from inherited defective genes. These genes can be detected by comparing the sequences of the defective gene with that of a normal one. Subsequently, one can verify that a "mutant" gene is associated with abnormal receptor activity. In addition, one can insert mutant receptor genes into a suitable vector for expression in a functional assay system (e.g., calorimetric assay, expression on MacConkey plates, complementation experiments, in a receptor deficient strain of HEK293 cells) as yet another means to verify or identify mutations. Once "mutant" genes have been identified, one can then screen population for carriers of the "mutant" receptor gene.

Individuals carrying mutations in the gene of the present invention may be detected at the DNA level by a variety of techniques. Nucleic acids used for diagnosis may be obtained from a patient's cells, including but not limited to such as from blood, urine, saliva, tissue biopsy and autopsy material. The genomic DNA may be used directly for detection or may be amplified enzymatically by using PCR (Saiki, et al., *Nature*, 324:163–166 1986) prior to analysis. RNA or cDNA may also be used for the same purpose. As an example, PCR primers complimentary to the nucleic acid of the instant invention can be used to identify and analyze mutations in the gene of the present invention. For example, deletions and insertions can be detected by a change in size of the amplified product in comparison to the normal genotype. Point mutations can be identified by hybridizing amplified DNA to radio labeled RNA of the invention or alternatively, radio labeled antisense DNA sequences of the invention. Perfectly matched sequences can be distinguished from mismatched duplexes by RNase A digestion or by differences in melting temperatures. Such a diagnostic would be particularly useful for prenatal or even neonatal testing.

Sequence differences between the reference gene and "mutants" may be revealed by the direct DNA sequencing method. In addition, cloned DNA segments may be used as probes to detect specific DNA segments. The sensitivity of this method is greatly enhanced when combined with PCR. For example, a sequence primer is used with double stranded PCR product or a single stranded template molecule generated by a modified PCR. The sequence determination is performed by conventional procedures with radio labeled nucleotide or by an automatic sequencing procedure with fluorescent-tags.

Genetic testing based on DNA sequence differences may be achieved by detection of alterations in the electrophoretic mobility of DNA fragments in gels with or without denaturing agents. Sequences changes at specific locations may also be revealed by nucleus protection assays, such RNase and S1 protection or the chemical cleavage method (e.g. Cotton, et al., *PNAS, USA*, 85:4397–4401 1985).

In addition, some diseases are a result of, or are characterized by changes in gene expression which can be detected by changes in the mRNA. Alternatively, the genes of the present invention can be used as a reference to identify individuals expressing a decrease of functions associated with receptors of this type.

The present invention also relates to a diagnostic assay for detecting altered levels of soluble forms of the receptor polypeptides of the present invention in various tissues. Assays used to detect levels of the soluble receptor polypeptides in a sample derived from a host are well known to those of skill in the art and include radioimmunoassays, competitive-binding assays, Western blot analysis and preferably as ELISA assay.

An ELISA assay initially comprises preparing an antibody specific to antigens of the receptor polypeptides, preferably a monoclonal antibody. In addition a reporter antibody is prepared against the monoclonal antibody. To the reporter antibody is attached a detectable reagent such as radioactivity, fluorescence or in this example a horseradish peroxidase enzyme. A sample is now removed from a host and incubated on a solid support, e.g. a polystyrene dish, that binds the proteins in the sample. Any free protein binding sites on the dish are then covered by incubating with a non-specific protein such as bovine serum albumin. Next, the monoclonal antibody is incubated in the dish during which time the monoclonal antibodies attach to any RARε receptor proteins attached to the polystyrene dish. All unbound monoclonal antibody is washed out with buffer. The reporter antibody linked to horseradish peroxidase is now placed in the dish resulting in binding of the reporter antibody to any monoclonal antibody bound to RARε receptor proteins. Unattached reporter antibody is then washed out. Peroxidase substrates are then added to the dish and the amount of color developed in a given time period is a measurement of the amount of RARε receptor proteins present in a given volume of patient sample when compared against a standard curve.

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with genes associated with disease.

Briefly, sequences can be mapped to chromosomes by preparing PCR primers (preferably 15–25 bp) from the cDNA. Computer analysis of the cDNA is used to rapidly select primers that do not span more than one exon in the genomic DNA, thus complicating the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can similarly be used to map to its chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNA as short as 50 or 60 bases. For a review of this technique, see Verma et al., *Human Chromosomes: a Manual of Basic Techniques*, Pergamon Press, New York (1988).

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes. (This assumes 1 megabase mapping resolution and one gene per 20 kb).

The polypeptides, their fragments or other derivatives, or analogs thereof, or cells expressing them can be used as an immunogen to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against the polypeptides corresponding to a sequence of the present invention can be obtained by direct injection of the polypeptides into an animal or by administering the polypeptides to an animal, preferably a nonhuman. The antibody so obtained will then bind the polypeptides itself. In this manner, even a sequence encoding only a fragment of the polypeptides can be used to generate antibodies binding the whole native polypeptides. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler and Milstein, 1975, Nature, 256:495–497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77–96).

Techniques described for the production of single chain antibodies (U.S. Pat. No. 4,946,778) can be adapted to produce single chain antibodies to immunogenic polypeptide products of this invention. Also, transgenic mice may be used to express humanized antibodies to immunogenic polypeptide products of this invention.

The present invention will be further described with reference to the following examples; however, it is to be understood that the present invention is not limited to such examples. All parts or amounts, unless otherwise specified, are by weight.

In order to facilitate understanding of the following examples certain frequently occurring methods and/or terms will be described.

"Plasmids" are designated by a lower case p preceded and/or followed by capital letters and/or numbers. The starting plasmids herein are either commercially available, publicly available on an unrestricted basis, or can be constructed from available plasmids in accord with published procedures. In addition, equivalent plasmids to those described are known in the art and will be apparent to the ordinarily skilled artisan.

"Digestion" of DNA refers to catalytic cleavage of the DNA with a restriction enzyme that acts only at certain sequences in the DNA. The various restriction enzymes used herein are commercially available and their reaction conditions, cofactors and other requirements were used as would be known to the ordinarily skilled artisan. For analytical purposes, typically 1 $\mu$g of plasmid or DNA fragment is used with about 2 units of enzyme in about 20 $\mu$l of buffer solution. For the purpose of isolating DNA fragments for plasmid construction, typically 5 to 50 $\mu$g of DNA are digested with 20 to 250 units of enzyme in a larger volume. Appropriate buffers and substrate amounts for particular restriction enzymes are specified by the manufacturer. Incubation times of about 1 hour at 37° C. are ordinarily used, but may vary in accordance with the supplier's instructions. After digestion the reaction is electrophoresed directly on a polyacrylamide gel to isolate the desired fragment.

Size separation of the cleaved fragments is performed using 8 percent polyacrylamide gel described by Goeddel, D. et al., Nucleic Acids Res., 8:4057 (1980).

"Oligonucleotides" refers to either a single stranded polydeoxynucleotide or two complementary polydeoxynucleotide strands which may be chemically synthesized. Such synthetic oligonucleotides have no 5' phosphate and thus will not ligate to another oligonucleotide without adding a phosphate with an ATP in the presence of a kinase. A synthetic oligonucleotide will ligate to a fragment that has not been dephosphorylated.

"Ligation" refers to the process of forming phosphodiester bonds between two double stranded nucleic acid fragments (Maniatis, T., et al., Id., p. 146). Unless otherwise provided, ligation may be accomplished using known buffers and conditions with 10 units to T4 DNA ligase ("ligase") per 0.5 $\mu$g of approximately equimolar amounts of the DNA fragments to be ligated.

Unless otherwise stated, transformation was performed as described in the method of Graham, F. and Van der Eb, A., Virology, 52:456–457 (1973).

EXAMPLE 1

Expression of RARε By In Vitro Transcription And Translation

Figure 4:
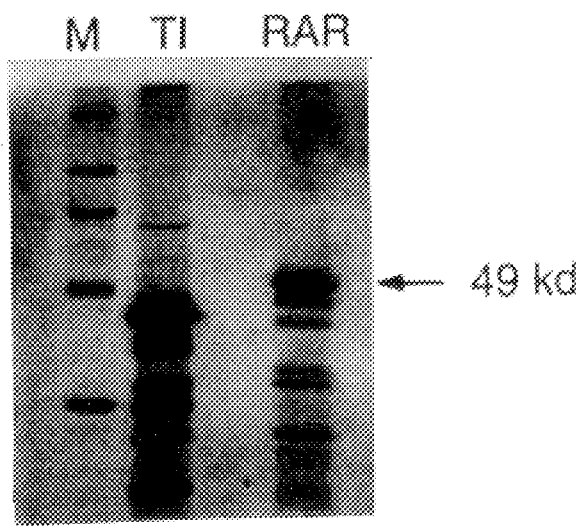
FIG. 4 shows the results of electrophoresing RARε on a gel after in vitro transcription/translation.

The in vitro transcription and translation of RARε was carried out using the TNT Coupled Reticulocyte Lysate System (Promega, 2800 Woods Hollow Road, Madison, Wis. 53771-5399). The cDNA encoding for RARε, ATCC # 75754, was cloned directionally EcoRI to XhoI with the EcoRI site defining the 5' end of the gene and the XhoI site defining the 3' end of the gene. The gene was inserted in the T3 direction. T3 defines a bacteriophage RNA polymerase which recognizes a specific promoter, and transcribes the DNA into a mRNA. A rabbit reticulocyte lysate is supplemented with T3 RNA polymerase and directs the expression of proteins with a T3 promoter utilizing the T3 RNA polymerase to transcribe the message, and the reticulocyte lysate to translate the nascent RNA. 1 $\mu$g of circular (or linear) plasmid containing the RARε DNA was added directly to TNT™ lysate and incubated in a 50 $\mu$l reaction volume at 30° C. for 1 hour with T3 RNA polymerase and [$^{35}$S]-Methionine. After incubation, the translation product was separated by 10% SDS-PAGE gel electrophoresis. The gel was fixed in 10% acetic acid, 15% methanol for 30 minutes followed by drying on a Bio-Rad gel dryer for one hour. Autoradiography was carried out with Kodak XAR film. The film was exposed at −80° C. with intensifying screen. A prominent translation product is visible at 49 kd (FIG. 4).

EXAMPLE 2
Expression and Purification of RARε In Baculovirus-insect cell system Sf9 insect cells are maintained in culture using Grace's Insect medium (Gibco) supplemented with 10% FBS at 27° C. The baculovirus transfer plasmid pA2 was constructed by Gentz et al (unpublished results) (FIG. 5). The entire human RARE cDNA including the BamHl site at 5' end and Asp 718 site at 3' end were amplified using PCR. The PCR oligonucleotide primers used for the amplification of the human RARε are:

5'-GCGCGGATCCACCATGTCCTTGTGGCTGGGG-3' (SEQ ID NO:3)

5'-GCGCGGTACCTCATTCGTGCACATCCCAGAT-3' (SEQ ID NO:4).

The amplified fragment containing human RARε cDNA, and plasmid pA2 were digested by BamHI and Asp 718 and purified by Geneclean kit. The amplified fragment containing human RARε cDNA was inserted into vector pA2 to generate the recombinant transfer vector pA2RARε. The accuracy of the construct was verified using restriction endonuclease, PCR and DNA sequencing. Transfer of the human RARε cDNA from and pA2RAR to an AcNPV genome can be achieved by co-transfection using Lipofectin (Gibco). AcNPV is a wild-type virus abailable from Pharmagene (San Diego, Calif.). Techniques for manipulation of baculovirus and insect cell culture such as cultivation, co-transfection, virus infection, isolation, screening and purification of putative recombinant plaques and virus titer determination was described by O'Reilly D. R. et al [Baculovirus expression vectors: A Laboratory Manual (1992), W. H. Freeman and Company]. The plaques will be screened for recombinant baculovirus by using the blue-white selection. The visually screened plaques are to be analyzed and confirmed by PCR screening. Once the recombinant virus is obtained, Sf9 cells ($2 \times 10^6$ cells/ml) can be infected with recombinant RAR virus ($10^8$ plaque-forming units/ml) for 2 hr at room temperature. After transfection, the viral inoculum is replaced with fresh medium. The supernatant and cells are harvested after 60–72 hr. The extra cellular and intracellular fractions are then analyzed for the expression of RARε by SDS-PAGE. The receptor can be partially purified by sequential anion-exchange, gel-filtration and DNA affinity chromatography.

EXAMPLE 3
Expression Pattern of RARε In Human Tissue

Figure 3:
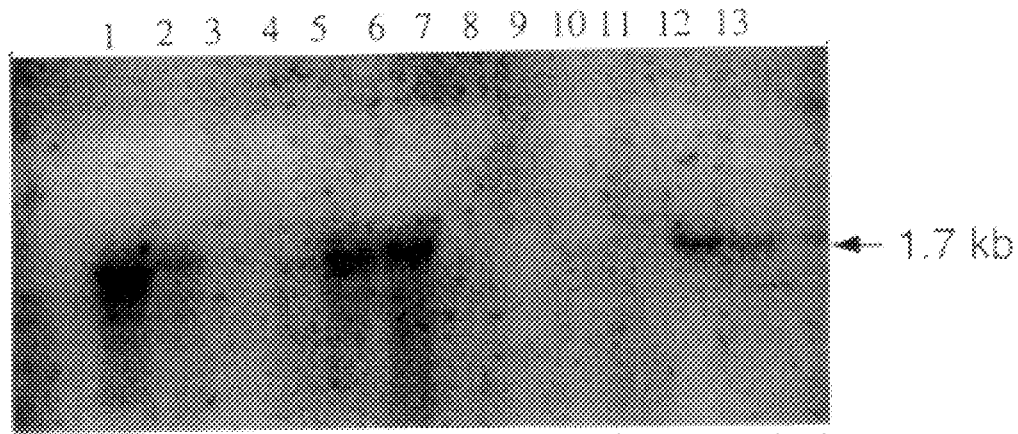
FIG. 3 depicts the results of a Northern blot analysis of the gene of the present invention in human adult tissues.

Northern blot analysis was carried out to examine the levels of expression of RARε in human tissues. Total cellular RNA samples were isolated with RNAzol™ B system (Biotecx Laboratories, Inc. 6023 South Loop East, Houston, Tex. 77033). About 10 μg of total RNA isolated from each human tissue specified was separated on 1% agarose gel and blotted onto a nylon filter. (Sambrook, Fritsch, and Maniatis, Molecular Cloning, Cold Spring Harbor Press, (1989)). The labeling reaction was done according to the Stratagene Prime-It kit with 50 ng DNA fragment. The labeled DNA was purified with a Select-G-50 column. (5 Prime - 3 Prime, Inc. 5603 Arapahoe Road, Boulder, Colo. 80303). The filter was then hybridized with radioactive labeled full length RARε gene at 1,000,000 cpm/ml in 0.5M NaPO$_4$, pH 7.4 and 7% SDS overnight at 65° C. After wash twice at room temperature and twice at 60° C. with 0.5× SSC, 0.1% SDS, the filter was then exposed at −70° C. overnight with an intensifying screen. The message RNA for RARε is abundant in testes, placenta, spleen, thymus and lung. (FIG. 3).

EXAMPLE 4
Expression Via Gene Therapy

Fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin, is added. This is then incubated at 37° C. for approximately one week. At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al, DNA, 7:219–25 (1988) flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding a polypeptide of the present invention is amplified using PCR primers which correspond to the 5' and 3' end sequences respectively. The 5' primer containing an EcoRI site and the 3' primer having contains a HindIII site. Equal quantities of the Moloney murine sarcoma virus linear backbone and the EcoRI and HindIII fragment are added together, in the presence of T4 DNA ligase. The resulting mixture is maintained under conditions appropriate for ligation of the two fragments. The ligation mixture is used to transform bacteria HB101, which are then plated onto agar-containing kanamycin for the purpose of confirming that the vector had the gene of interest properly inserted.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the gene is then added to the media and the packaging cells are transduced with the vector. The packaging cells now produce infectious viral particles containing the gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his.

The engineered fibroblasts are then injected into the host, either alone or after having been grown to confluence on cytodex 3 microcarrier beads. The fibroblasts now produce the protein product.

Numerous modifications and variations of the present invention are possible in light of the above teachings and, therefore, within the scope of the appended claims, the invention may be practiced otherwise than as particularly described.

What is claimed is:

1. An isolated polynucleotide comprising a polynucleotide having at least 95% identity to a member selected from the group consisting of:
   (a) a polynucleotide encoding a polypeptide comprising amino acid 2 to 433 of SEQ ID NO:2; and
   (b) the complement of (a).

2. The isolated polynucleotide of claim 1 wherein said member is (a).

3. The isolated polynucleotide of claim 1 wherein said member is (a) and the polypeptide comprises amino acids 1 to 433 of SEQ ID NO:2.

4. The isolated polynucleotide of claim 1 comprising a polynucleotide encoding a polypeptide comprising the amino acid sequence identical to amino acids 2 to 433 of SEQ ID NO:2.

5. The isolated polynucleotide of claim 1, wherein the polynucleotide is DNA.

6. The isolated polynucleotide of claim 1 comprising a polynucleotide encoding a polypeptide comprising the amino sequence identical to amino acids 1 to 433 of SEQ ID NO:2.

7. The isolated polynucleotide of claim 1, wherein said polynucleotide is RNA.

8. A method of making a recombinant vector comprising inserting the isolated polynucleotide of claim 2 into a vector, wherein said polynucleotide is DNA.

9. A recombinant vector comprising the polynucleotide of claim 2, wherein said polynucleotide is DNA.

10. A recombinant host cell comprising the polynucleotide of claim 2, wherein said polynucleotide is DNA.

11. A method for producing a polypeptide comprising expressing from the recombinant cell of claim 10 the polypeptide encoded by said polynucleotide and isolated said polypeptide.

12. A process for producing a polypeptide comprising:
   expressing from a recombinant cell containing the polynucleotide of claim 4 the polypeptide encoded by said polynucleotide and isolating said polypeptide.

13. A process for producing a polypeptide comprising:
   expressing from a recombinant cell containing the polynucleotide of claim 6 the polypeptide encoded by said polynucleotide and isolating said polypeptide.

14. The isolated polynucleotide of claim 4 comprising nucleotides 183 to 1478 of SEQ ID NO:1.

15. The isolated polynucleotide of claim 4 comprising nucleotides 180 to 1478 of SEQ ID NO:1.

16. The isolated polynucleotide of claim 4 comprising the nucleotides of the sequence of SEQ ID NO:1.

17. An isolated polynucleotide comprising the nucleotides of SEQ ID NO:1 coding for the mature retinoid acid receptor epsilon (RARε) protein.

18. An isolated polynucleotide comprising a polynucleotide having at least a 95% identity to a member selected from the group consisting of:

(a) a polynucleotide encoding the same mature polypeptide encoded by the human cDNA in ATCC Deposit No. 75754; and (b) the complement of (a).

19. The isolated polynucleotide of claim 18, wherein the member is (a).

20. The isolated polynucleotide of claim 18, wherein said polynucleotide comprises DNA identical to the coding portion of the human cDNA in ATCC Deposit No 75754 which encodes a mature polypeptide.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
    ( A ) LENGTH: 1649 BASE PAIRS
    ( B ) TYPE: NUCLEIC ACID
    ( C ) STRANDEDNESS: SINGLE
    ( D ) TOPOLOGY: LINEAR ( i i ) MOLECULE TYPE: cDNA ( x i ) SEQUENCE DESCRIPTION: SEQ ID NO:1:

```
AGTCCAGGTC   CTGCTTGTGC   TCAGCTCCAG   CTCACTGGCT   GGCCACCGAA   ACTTCTGGAC     60
AGGAAACTGC   ACCATCCTCT   TCTCCCAGCA   AGGGGGCTCC   AGAGAACTGC   CCACCCAGGA    120
AGTCTGGTGG   CCTGGGGATT   TGGACAGTGC   CTTGGTAATG   ACCAGGGCTC   CAGGAAGAGA    180
TGTCCTTGTG   GCTGGGGGCC   CCTGTGCCTG   ACATTCCTCC   TGACTCTGCG   GTGGAGCTGT    240
GGAAGCCAGG   CGCACAGGAT   GCAGGCAGCC   AGGCCCAGGG   AGGCAGCAGC   TGCATCCTCA    300
GAGAGGAAGC   CAGGATGCCC   CACTCTGCTG   GGGGTACTGC   AGGGGTGGGG   CTGGAGGCTG    360
CAGAGCCCAC   AGCCCTGCTC   ACCAGGGCAG   AGCCCCCTTC   AGAACCCACA   GAGATCCGTC    420
CACCAAAGCG   GAAAAAGGGG   CCAGCCCCCA   AAATGCTGGG   GAACGAGCTA   TGCAGCGTGT    480
GTGGGGACAA   GGCCTCGGGC   TTCCACTACA   ATGTTCTGAG   CTGCGAGGGC   TGCAAGGAAT    540
TCTTCCGCCG   CAGCGTCATC   AAGGGAGCGC   ACTACATCTG   CCACAGTGGC   GGCCACTGCC    600
CATGGAACAC   CTACATGCGT   CGCAAGTGCC   AGGAGTGTGT   CCTGTCAGAA   GAACAGATCC    660
GCCTGAAGAA   ACTGAAGCGG   CAAGAGGAGG   AACAGGTTCA   TGCCACATCC   TTGCCCCCA    720
GGGCTTCCTC   ACCCCCCCAA   ATCCTGCCCC   AGCTCAACCC   GGAACAACTG   GCATGATCG    780
AGAAGCTCGT   CCCTGCCCAG   CAACAGTGTA   ACCGGCGCTC   CTTTTCTGAC   CGGCTTCGAG    840
TCACGCCTTG   GCCCATGGCA   CCAGATCCCC   ATAGCCGGGA   GGCCCGTCAG   CAGCGCTTTG    900
CCCACTTCAC   TGAGCTGGCC   ATCGTCTCTG   TGCAGGAGAT   AGTTGACTTT   GCTAAACAGC    960
TACCCGGCTT   CCTGCAGCTC   AGCCGGGAGG   ACCAGATTGC   CCTGCTGAAG   ACCTCTGCGA   1020
TCGAGGTGAT   GCTTGTGGAG   ACATCTCGGA   GGTACAACCC   TGGGAGTGAG   AGTATCACCT   1080
TCCTCAAGGA   TTTCAGTTAT   AACCGGGAAG   ACTTTGCCAA   AGCAGGGCTG   CAAGTGGAAT   1140
TCATCAACCC   CATCTTCGAG   TTCTCCAGGG   CCATGAATGA   GCTGCAACTC   AATGATCCCG   1200
AGTTTGCCTT   GCTCATTGCT   ATCAGCATCT   TCTCTGCAGA   CCGGCCCAAC   GTGCAGGACC   1260
AGCTCCAGGT   AGAGAGGCTG   CAGCACACAT   ATGTGGAAGC   CCTGCATGCC   TACGTCTCCA   1320
TCCACCATCC   CCATGACCGA   CTGATGTTCC   CACGGATGCT   AATGAAACTG   GTGAGCCTCC   1380
GGACCCTGAG   CAGCGTCCAC   TCAGAGCAAG   TGTTTGCACT   GCGTCTGCAG   GACAAAAAGC   1440
TCCCACCGCT   GCTCTCTGAG   ATCTGGGATG   TGCACGAATG   ACTGTTCTGT   CCCCATATTT   1500
TCTGTTTTCT   TGGCCGGATG   GCTGAGGCCT   GGTGGCTGCC   TCCTAGAAGT   GGAACAGACT   1560
GAGAAGGGCA   AACATTCCTG   GGAGCTGGGA   AAGGAGATCC   TCCCGTGGCA   TTAAAAGAGA   1620
GTCAAAGGGT   AAAAAAAAAA   AAAAAAAA                                          1649
```

( 2 ) INFORMATION FOR SEQ ID NO:2:

( i ) SEQUENCE CHARACTERISTICS:
    ( A ) LENGTH: 433 AMINO ACIDS (B) TYPE: AMINO ACID
(C) STRANDEDNESS:
(D) TOPOLOGY: LINEAR (ii) MOLECULE TYPE: PROTEIN (xi) SEQUENCE DESCRIPTION: SEQ ID NO:2:

```
Met  Ser  Leu  Trp  Leu  Gly  Ala  Pro  Val  Pro  Asp  Ile  Pro  Pro  Asp
 5                  10                      15

Ser  Ala  Val  Glu  Leu  Trp  Lys  Pro  Gly  Ala  Gln  Asp  Ala  Gly  Ser
20                  25                      30

Gln  Ala  Gln  Gly  Gly  Ser  Ser  Cys  Ile  Leu  Arg  Glu  Glu  Ala  Arg
35                  40                      45

Met  Pro  His  Ser  Ala  Gly  Gly  Thr  Ala  Gly  Val  Gly  Leu  Glu  Ala
50                  55                      60

Ala  Glu  Pro  Thr  Ala  Leu  Leu  Thr  Arg  Ala  Glu  Pro  Pro  Ser  Glu
65                  70                      75

Pro  Thr  Glu  Ile  Arg  Pro  Lys  Arg  Lys  Lys  Gly  Pro  Ala  Pro
80                  85                      90

Lys  Met  Leu  Gly  Asn  Glu  Leu  Cys  Ser  Val  Cys  Gly  Asp  Lys  Ala
95                  100                     105

Ser  Gly  Phe  His  Tyr  Asn  Val  Leu  Ser  Cys  Glu  Gly  Cys  Lys  Glu
110                 115                     120

Phe  Phe  Arg  Arg  Ser  Val  Ile  Lys  Gly  Ala  His  Tyr  Ile  Cys  His
125                 130                     135

Ser  Gly  Gly  His  Cys  Pro  Trp  Asn  Thr  Tyr  Met  Arg  Arg  Lys  Cys
140                 145                     150

Gln  Glu  Cys  Val  Leu  Ser  Glu  Glu  Gln  Ile  Arg  Leu  Lys  Lys  Leu
155                 160                     165

Lys  Arg  Gln  Glu  Glu  Glu  Gln  Val  His  Ala  Thr  Ser  Leu  Pro  Pro
170                 175                     180

Arg  Ala  Ser  Ser  Pro  Pro  Gln  Ile  Leu  Pro  Gln  Leu  Asn  Pro  Glu
185                 190                     195

Gln  Leu  Gly  Met  Ile  Glu  Lys  Leu  Val  Pro  Ala  Gln  Gln  Gln  Cys
200                 205                     210

Asn  Arg  Arg  Ser  Phe  Ser  Asp  Arg  Leu  Arg  Val  Thr  Pro  Trp  Pro
215                 220                     225

Met  Ala  Pro  Asp  Pro  His  Ser  Arg  Glu  Ala  Arg  Gln  Gln  Arg  Phe
230                 235                     240

Ala  His  Phe  Thr  Glu  Leu  Ala  Ile  Val  Ser  Val  Gln  Glu  Ile  Val
245                 250                     255

Asp  Phe  Ala  Lys  Gln  Leu  Pro  Gly  Phe  Leu  Gln  Leu  Ser  Arg  Glu
260                 265                     270

Asp  Gln  Ile  Ala  Leu  Leu  Lys  Thr  Ser  Ala  Ile  Glu  Val  Met  Leu
275                 280                     285

Val  Glu  Thr  Ser  Arg  Arg  Tyr  Asn  Pro  Gly  Ser  Glu  Ser  Ile  Thr
290                 295                     300

Phe  Leu  Lys  Asp  Phe  Ser  Tyr  Asn  Arg  Glu  Asp  Phe  Ala  Lys  Ala
305                 310                     315

Gly  Leu  Gln  Val  Glu  Phe  Ile  Asn  Pro  Ile  Phe  Glu  Phe  Ser  Arg
320                 325                     330

Ala  Met  Asn  Glu  Leu  Gln  Leu  Asn  Asp  Pro  Glu  Phe  Ala  Leu  Leu
335                 340                     345

Ile  Ala  Ile  Ser  Ile  Phe  Ser  Ala  Asp  Arg  Pro  Asn  Val  Gln  Asp
350                 355                     360
```

|     |     |     |     |     |     |     |     |     |     |     |     |     |     |     |
|-----|-----|-----|-----|-----|-----|-----|-----|-----|-----|-----|-----|-----|-----|-----|
| Gln | Leu | Gln | Val | Glu | Arg | Leu | Gln | His | Thr | Tyr | Val | Glu | Ala | Leu |
| 365 |     |     |     |     | 370 |     |     |     |     | 375 |     |     |     |     |
| His | Ala | Tyr | Val | Ser | Ile | His | His | Pro | His | Asp | Arg | Leu | Met | Phe |
| 380 |     |     |     |     | 385 |     |     |     |     | 390 |     |     |     |     |
| Pro | Arg | Met | Leu | Met | Lys | Leu | Val | Ser | Leu | Arg | Thr | Leu | Ser | Ser |
| 395 |     |     |     |     | 400 |     |     |     |     | 405 |     |     |     |     |
| Val | His | Ser | Glu | Gln | Val | Phe | Ala | Leu | Arg | Leu | Gln | Asp | Lys | Lys |
| 410 |     |     |     |     | 415 |     |     |     |     | 420 |     |     |     |     |
| Leu | Pro | Pro | Leu | Leu | Ser | Glu | Ile | Trp | Asp | Val | His | Glu |     |     |
| 425 |     |     |     |     | 430 |     |     |     |     |     |     |     |     |     |

(2) INFORMATION FOR SEQ ID NO:3:

(i) SEQUENCE CHARACTERISTICS:
        (A) LENGTH: 31 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:3:

GCGCGGATCC ACCATGTCCT TGTGGCTGGG G    31

(2) INFORMATION FOR SEQ ID NO:4:

(i) SEQUENCE CHARACTERISTICS:
        (A) LENGTH: 31 BASE PAIRS
        (B) TYPE: NUCLEIC ACID
        (C) STRANDEDNESS: SINGLE
        (D) TOPOLOGY: LINEAR (ii) MOLECULE TYPE: Oligonucleotide (xi) SEQUENCE DESCRIPTION: SEQ ID NO:4:

GCGCGGTACC TCATTCGTGC ACATCCAGA T    31